United States Patent
Zhang et al.

(10) Patent No.: US 11,747,426 B2
(45) Date of Patent: Sep. 5, 2023

(54) VALIDATION OF QUANTITATIVE MAGNETIC RESONANCE IMAGING PROTOCOLS

(71) Applicant: Oxford University Innovation Limited, Oxford (GB)

(72) Inventors: Qiang Zhang, Oxford (GB); Stefan Piechnik, Oxford (GB); Konrad Werys, Oxford (GB); Iulia Andreia Popescu, Oxford (GB); Vanessa Ferreira, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 17/611,346

(22) PCT Filed: May 15, 2020

(86) PCT No.: PCT/GB2020/051189
§ 371 (c)(1),
(2) Date: Nov. 15, 2021

(87) PCT Pub. No.: WO2020/234570
PCT Pub. Date: Nov. 26, 2020

(65) Prior Publication Data
US 2022/0229142 A1     Jul. 21, 2022

(30) Foreign Application Priority Data
May 17, 2019  (GB) ..................... 1906981

(51) Int. Cl.
G01R 33/58   (2006.01)
A61B 5/055   (2006.01)
G01R 33/50   (2006.01)

(52) U.S. Cl.
CPC .............. G01R 33/58 (2013.01); A61B 5/055 (2013.01); G01R 33/50 (2013.01)

(58) Field of Classification Search
None
See application file for complete search history.

(56) References Cited

U.S. PATENT DOCUMENTS 9,747,789 B2   8/2017  Griswold et al.
10,078,124 B2  9/2018  Horkay et al.
(Continued)

FOREIGN PATENT DOCUMENTS

WO   2019/145382 A1   8/2019

OTHER PUBLICATIONS

International Search Report and Written Opinion for WO 2020/234570 (PCT/GB2020/051189), dated Sep. 2, 2020, pp. 1-18.
(Continued)

Primary Examiner — Rodney E Fuller
(74) Attorney, Agent, or Firm — Thomas|Horstemeyer, LLP

(57) ABSTRACT

A validation technique for quality assurance of quantitative MRI methods by comparing the measured magnetic properties of a phantom having a range of T1 and T2 values measured by an accelerated, clinically-practicable protocol with predicted values for that magnetic property calculated from a set of reference T1 and T2 values measured on the phantom. The prediction is based on a relationship between the values from the accelerated protocol and values from the reference measurements obtained by repeatedly scanning one or more phantoms.

16 Claims, 13 Drawing Sheets

(56) References Cited

U.S. PATENT DOCUMENTS

| | | | |
|---|---|---|---|
| 2014/0292330 | A1 | 10/2014 | Gulani et al. |
| 2020/0348384 | A1 | 11/2020 | Bickelhaupt et al. |
| 2021/0166384 | A1* | 6/2021 | Geethanath ............ G16H 50/20 |
| 2021/0177261 | A1* | 6/2021 | Geethanath ........... A61B 5/0042 |
| 2022/0001043 | A1* | 1/2022 | Wilson ............... A61K 51/1069 |

OTHER PUBLICATIONS

UK Search Report for GB 1906981.4, dated Oct. 31, 2019, pp. 1-3.
Chow, Kevin et al.: "An Analytic Description of Factors Affecting MOLLI Is Accuracy Using a Time-Weighted Average Model of TI Relaxation", International Society for Magnetic Resonance in Medicine, ISMRM, 2030 Addison Street, 7th Floor, Berkeley, CA 94704 USA, No. 2453, Apr. 28, 2014 (Apr. 28, 2014).
Peter Kellman et al: "Adiabatic inversion pulses for myocardial TI mapping", Magnetic Resonance in Medicine., vol. 71, No. 4, May 30, 2013 (May 30, 2013), pp. 1428-1434.
Fabio S Raman et al: "Modified look-locker inversion recovery TI mapping indices: assessment of accuracy and reproducibility between magnetic resonance scanners", Journal of Cardiovascular Magnetic Resonance, Biomed Central Ltd, London UK, vol. 15, No. 1, Jul. 26, 2013 (Jul. 26, 2013), p. 64.
Piechnik SK et al., 'Myocardial T1 mapping and extracellular vol. quantification: an overview of technical and biological confounders', Int. J Cardiovasc. Imaging. Jan. 2018; 34(1):3-14 doi: 10.1007/s10554-017-1235-7. Epub Aug. 28, 2017.
Taylor et al., "T1 Mapping: Basic Techniques and Clinical Applications", JACC: Cardiovascular Imaging, vol. 9, Issue 1, Jan. 2016, pp. 67-81.
Ma D., Gulani et al., "Magnetic Resonance Fingerprinting" Nature, 2013; 495:187-192.
Mehta et al., "Magnetic resonance fingerprinting: a technical review", Magn Reson Med . 2019;81:25-46.
European Society of Radiology, Magnetic Resonance Fingerprinting—a promising new approach to obtain standardized imaging biomarkers from MRI, Insights Imaging (2015) 6:163-165.

* cited by examiner

Fig. 5

| | | |
|---|---|---|
| 1 | Copy all protocol below in one go | |
| 2 | Name=HCMRPhantomID### Temper... | |
| 3 | Set up ECG 60bpm | |
| 4 | Localiser ISO | 00:09 |
| 5 | Check HCMR phantom is in the ISO ce... | |
| 6 | Now wait > 15 seconds | |
| 7 | ShMOLLI_WIP448C | 00:09 |
| 8 | Now wait > 15 seconds | |
| 9 | ShMOLLI_WIP448C | 00:09 |
| 10 | Now wait > 15 seconds | |
| 11 | ShMOLLI_WIP448C | 00:09 |
| 12 | Now wait > 15 seconds | |
| 13 | ShMOLLI_WIP448C | 00:09 |
| 14 | Now wait > 15 seconds | |
| 15 | ShMOLLI_WIP448C | 00:09 |
| 16 | Remaining scans can run unsupervised | |
| 17 | se_multiecho-TR2000 | 08:38 |
| 18 | se_multiecho-TR2000-PhSwap | 08:38 |
| 19 | refTSE_TF7_TI33 | 06:22 |
| 20 | refTSE_TF7_TI100 | 06:22 |
| 21 | refTSE_TF7_TI300 | 06:22 |
| 22 | refTSE_TF7_TI900 | 06:22 |
| 23 | refTSE_TF7_TI2700 | 06:22 |
| 24 | refTSE_TF7_TI5000 | 06:22 |
| 25 | refTSE_TF2_TI5000 | 21:32 |
| 26 | refTSE_TF2_TI2700 | 21:32 |
| 27 | refTSE_TF2_TI900 | 21:32 |
| 28 | refTSE_TF2_TI300 | 21:32 |
| 29 | refTSE_TF2_TI100 | 21:32 |
| 30 | refTSE_TF2_TI33 | 21:32 |
| 31 | se_multiecho-TR9000 | 38:33 |

1-2 minutes of attention

~2-3 minutes set up as manual (but can be automated with voice commands)

check only first time these run and use the right coils when set up once, these scans can run unsupervised overnight

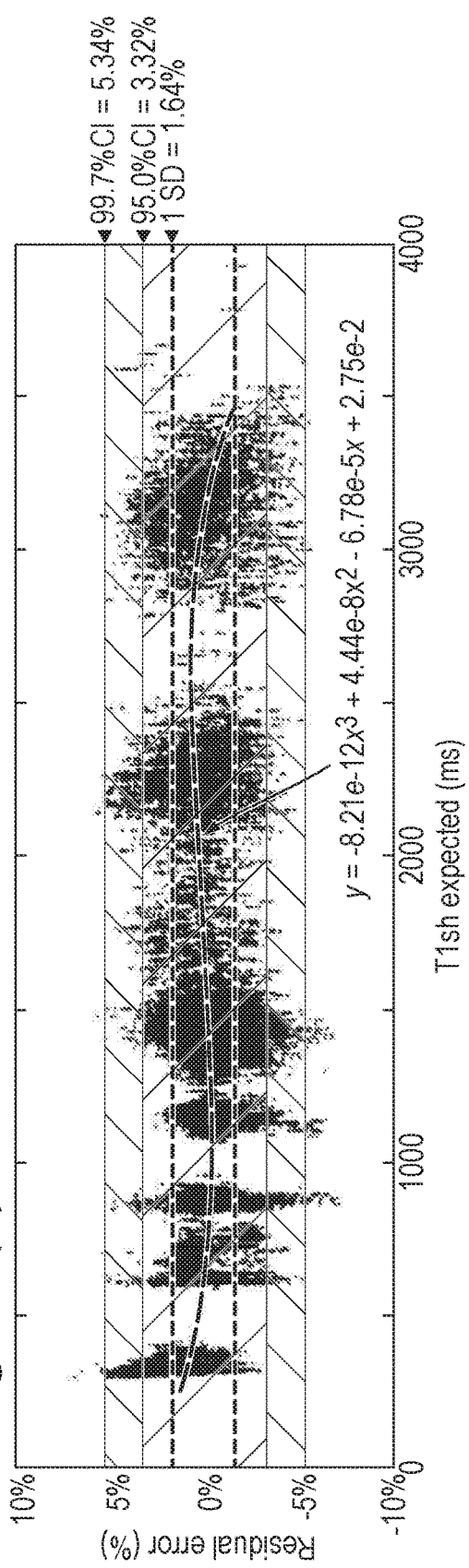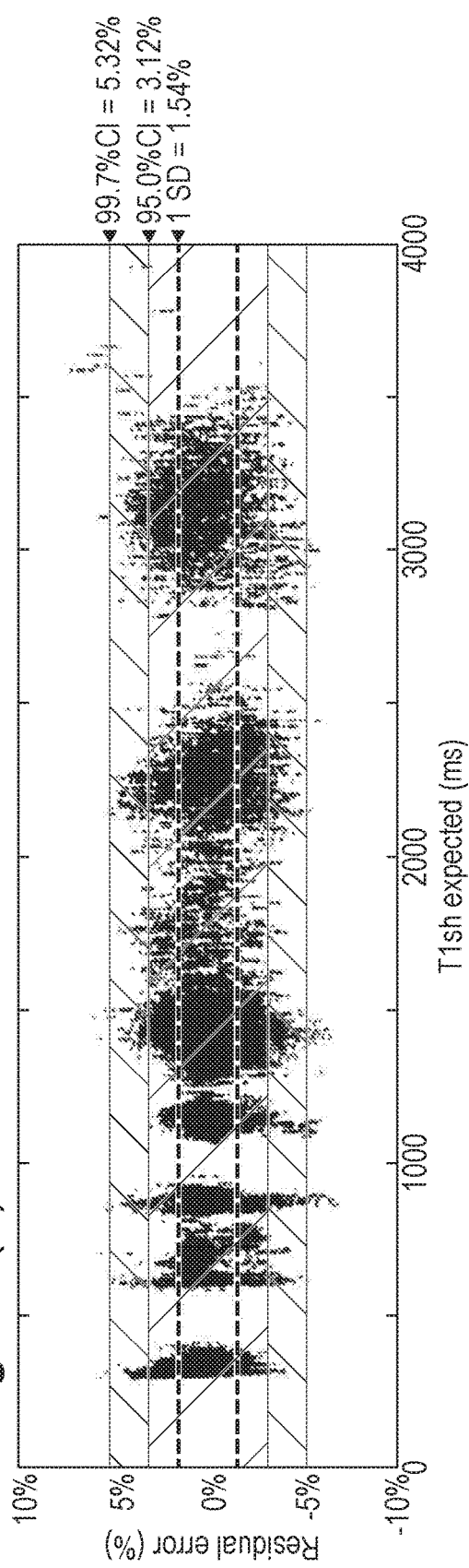
Fig. 10(a)
Fig. 10(b)

Fig. 11(c)
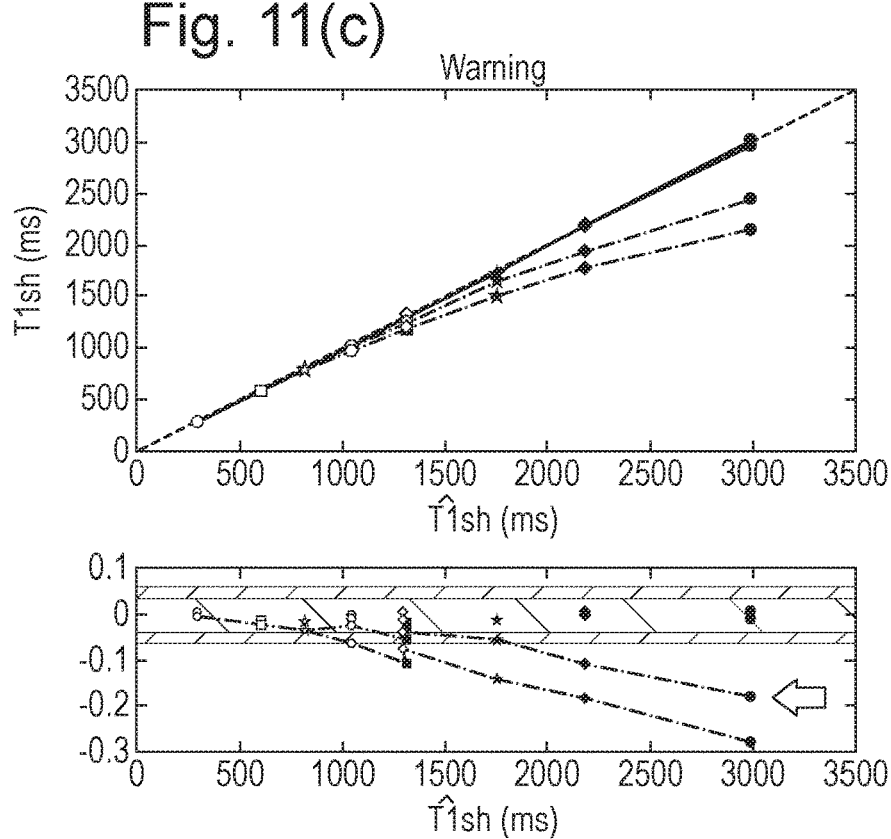
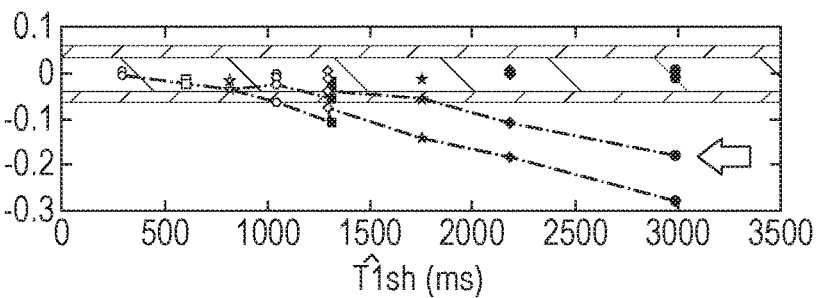
Fig. 11(d)
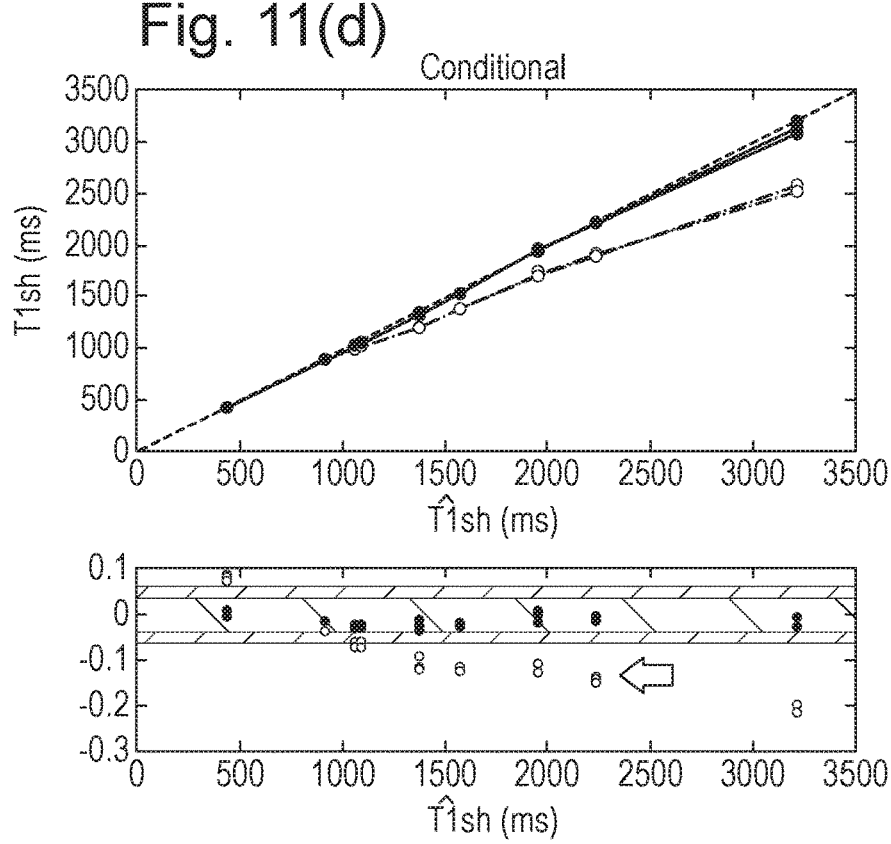
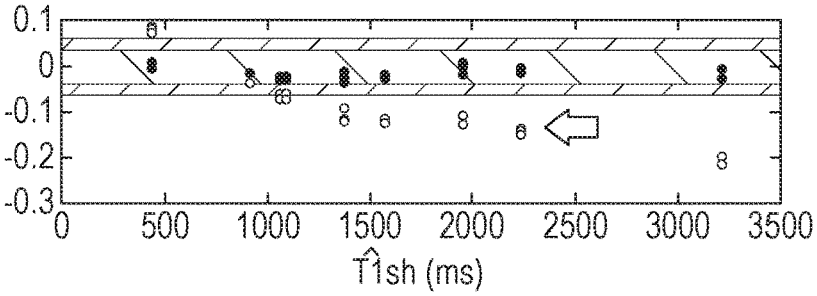

VALIDATION OF QUANTITATIVE MAGNETIC RESONANCE IMAGING PROTOCOLS

CROSS-REFERENCE TO RELATED APPLICATIONS

This application is the National Stage of International Application No. PCT/GB2020/051189, filed May 15, 2020, which claims priority to GB 1906981.4, filed May 17, 2019, which are entirely incorporated herein by reference.

The present invention relates to a method of validating, or quality-assuring, protocols used in quantitative magnetic resonance imaging.

Magnetic resonance (MR) imaging (MRI) has become ubiquitous as a medical imaging technique used to form images of a patient's anatomy and physiological processes within the patient's body for both healthy and diseased. In essence an MR image is a two dimensional display of the contrast arising from differences in multiple magnetic properties of the patient's tissue. Many different types of sequence, i.e. different combinations of static and oscillating magnetic fields and RF pulses, are well-known and often pre-programmed into MRI scanners in order to allow radiographers to choose the best sequence for detecting the tissue or tissue abnormality of interest for that particular patient. Such traditional sequences are weighted in a non-linear fashion towards multiple MR properties and depend on distances from the coils used to acquire the signal. In weighted MRI the differences across the plane of the image are of primary interest because these can be displayed and allow the visual recognition of tissue differences by a trained observer. Because the aim is to display an image which differentiates one sort of tissue from another, e.g. abnormal tissue from normal tissue, MRI has been used as a qualitative technique. Traditionally, no great interest has been put in the absolute (i.e. quantitative) value of the magnetic properties associated with the pixels in MRI images.

Further MRI sequences are known to measure directly the specific underlying magnetic properties of the substances, such as the spin-lattice relaxation time T1, the spin-spin-relaxation time T2, proton density (PD), etc. Thus interest has developed in so-called quantitative MRI with the aim of being able to characterise different tissue types or different abnormalities by their measured magnetic property, for example the actual T1 or T2 relaxation time or PD of that tissue. However a critical problem with this approach is that the measured value of the magnetic property depends sensitively on a variety of factors including MRI scanner, coil type, set-up, signal reconstruction, calibration, and so is not consistent from scan-to-scan or scanner-to-scanner. Often to study magnetic properties a tissue substitute called phantom is used. Even the most sophisticated phantoms cannot fully simulate the complexity of a living tissue. Living tissue consists of multiple levels of molecular, organellar, cellular and organ variability, with components exhibiting a range of magnetic properties. The measurement of MR properties is subject to dynamic exchange (by exchange of spin properties at molecular level and by flow and diffusion effects globally) during any practical length of the measurement time. Because of these factors ultimately no single MR property can ever accurately describe a complex mixture of various compartments in any biological system. As a result, any chosen quantification approach describes a weighted estimate of its principal target, and has been proven to be dependent on choices of particular sequence and their individual settings as used in the imaging process. Thus while quantitative MRI scans will give absolutely denominated quantitative values for various properties of the tissue, these values cannot be compared between different scans unless it is known that the protocols used in the scanning were the exactly the same.

In order to obtain clear MR images it is necessary for the patient to remain still during the MRI sequence. MRI sequences differ greatly in duration and, in general, the longer the duration the more difficult it is for a patient to remain still. Further, in some applications, such as cardiac MRI the patient's heartbeat and breathing significantly limit the clinically-acceptable duration for the sequence. Particular accelerated sequences have been developed which are of shorter duration than reference sequences and thus can be completed in a single breath hold for a patient, such as cardiac T1-mapping. These include, MOLLI, ShMOLLI, SASHA SAPPHIRE and many others (see for example: "Myocardial T1 mapping and extracellular volume quantification: an overview of technical and biological confounders", by Piechnik S K and Jerosch-Herold M., Int. J Cardiovasc. Imaging. 2018 January; 34(1):3-14. doi: 10.1007/s10554-017-1235-7. Epub 2017 Aug. 28, and "T1 Mapping: Basic Techniques and Clinical Applications" by Andrew J. Taylor MD, PhD, Michael Salerno MD, PhD, Rohan Dharmakumar PhD, Michael Jerosch-Herold PhD, JACC: Cardiovascular Imaging, Volume 9, Issue 1, January 2016, Pages 67-81).

These may be referred to as "clinically-practicable", or accelerated, MRI sequences. However, the values of the magnetic properties measured using such clinically-practicable sequences typically vary between each other and also vary from the values measured by longer-duration so-called "reference" sequences. This, therefore, again presents a significant difficulty in using clinically-practicable MRI sequences in quantitative MRI as the values do not necessarily allow quantitative comparisons across different scans and scanners for a consistent tissue characterisation by those values.

More recently a different approach known as Magnetic Resonance Fingerprinting (MRF) has been proposed. This involves a pseudorandomized multiparameter acquisition that causes the signals from different materials or tissues to have a unique signal evolution over time (or "fingerprint" that is simultaneously a function of the multiple material properties under investigation. The processing after acquisition involves a pattern recognition algorithm to match the fingerprints to a predefined dictionary of predicted signal evolutions. See, for example, "Magnetic Resonance Fingerprinting", MA D., Gulani V., Seiberlich N., et al., Nature, 2013; 495:187-192. However this does not itself guarantee that quantitative values measured in different scanners or centres are comparable.

If it could be guaranteed that MR scans follow the same protocol accurately, it would be possible to compare values measured in different scans and thus to characterise tissue by those values.

It is therefore an object of the present invention to provide a technique for quality assuring MRI scans by validating the protocols in use. This allows greater confidence that the measured values of the magnetic properties can be relied upon in tissue characterisation for comparisons between various centres or in time. The term "sequence" is generally used to refer to the combination of static and oscillating magnetic fields and RF pulses in order to obtain interpretable MR signal, and the term "protocol" to a set of one or more sequences with associated set-up requirements and possibly further steps such as pauses, set up of external conditions e.g. artificial triggering or timing of injection of contrast agents. An MR experiment is a procedure which is to be conducted according to a protocol and will include one or more sequences.

According to an aspect of the present invention, there is provided a method of validating a clinically-practicable MRI protocol comprising the steps of: conducting at least once a first, clinically-practicable, MRI experiment on a phantom to measure a first magnetic property of the phantom in accordance with the clinically-practicable MRI protocol to be validated; conducting a second, different MRI experiment on the phantom to measure a second magnetic property of the phantom; conducting a third MRI experiment on the phantom, the third MRI experiment being different from said first and second MRI experiments, to measure a third magnetic property of the phantom different from said first and second magnetic properties; calculating a predicted value of the first magnetic property from the measured second and third magnetic properties on the basis of a predetermined relationship between the first, second and third magnetic properties, calculating the difference between the predicted value of the first magnetic property and the measured value of the first magnetic property; determining that the MRI protocol used for said first MRI experiment was valid if the difference between the predicted value of the first magnetic property and the measured value of the first magnetic property is below a predetermined threshold; and outputting the result of the determination.

The predetermined relationship may be a non-linear, multi-parameter relationship, for example obtained by performing the measurements of the first, second and third magnetic properties multiple times, on the same or on a plurality of phantoms. The plurality of phantoms may vary in composition. The phantom(s) may include a plurality of materials whose magnetic properties differ to span a range of interest, for example, T1 and T2 values from 50 to 3500 ms.

The predetermined relationship may be obtained by performing the measurements of the first, second and third magnetic properties at two or more different magnetic field strengths. This is particularly useful if in practice MRI scans will be carried out at different field settings. For example, cardiac MRI is typically conducted at 1.5 T and 3.0 T. There may be one relationship independent of the magnetic field, individual relationships established for available choices of magnetic field, or one relationship (formula) where magnetic field is a parameter.

The predetermined relationship (which may be termed an "MR model") may be obtained by performing the measurements of the first, second and third magnetic properties at a plurality of different parameter values. Parameter values means variables, if any, which affect the relationship between the magnetic quantities being measured. For some magnetic quantities, e.g. ShMOLLI T1 (hereafter T1sh), the MR model is predominantly dependent on T1 and T2, with a slight difference between 1.5 T and 3 T. However for other clinically-practicable sequences, or where higher degree of accuracy in quality measures is desired, the model may be furnished with additional MR parameter dependencies (e.g. magnetization transfer, off-frequency characteristics, T2*, T1 rho, etc.) and experimental dependencies (e.g. heart rate or temperature at which measurements are performed). The desired MR model can be determined by conducting scans on the phantom at a variety of parameter values. For example, the relationship between MOLLI T1 and T1 is known to depend on heart rate, which would require an amendment in the model and the number of measurements to establish and validate it. Thus the further parameter values may comprise at least one of: temperature, magnetic transfer ratio, coil sensitivity, heart rate, MR frequency adjustment, etc.

The first and second magnetic properties may be the same, e.g. the spin-lattice relaxation time T1, but measured by two different approaches—at least one being a clinically-practicable or accelerated sequence, and the other being a set of other, typically longer duration reference experiments such as repeated turbo-spin-echo TSE acquisitions with varying inversion times. The third magnetic property may be the spin-spin relaxation time T2, measured with multiple TSE sequences varying TE, or one multi-echo acquisition to improve the speed. Typically the reference sequences would be simple and standard long-duration MR conventional techniques, such as to allow transparent and ease translation between various systems and manufacturers. The second and third experiment can also be achieved by a single hybrid sequence, such as magnetic resonance fingerprinting. Further, the first experiment can be within such a hybrid sequence.

The invention also provides a method of measuring a first magnetic property of human or animal tissue using an MRI protocol validated in accordance with the method above. This allows a quantitative MRI measurement in which there is greater confidence that the measured values are comparable to those from other sites or scan times, and thus are on a consistent basis. This allows the invention to extend to the step of characterising the tissue, e.g. as normal or abnormal, and the nature of the abnormality, according to the normal ranges for the measured first magnetic property being established globally, rather than at each individual centre.

According to further aspects of the present invention, there are provided a computer program capable of execution by a computer apparatus and configured, on execution, to cause the computer apparatus to perform a similar method, a computer-readable storage medium storing such a computer program, and a computer apparatus arranged to perform a similar method.

The invention will be further described by way of examples with reference to the accompanying drawings in which:

FIGS. 1(a) to (d) are different views of an example of a phantom for use in a methods of embodiments of the invention;

FIG. 2 is a flow diagram illustrating a quality assurance technique according to a first embodiment of the invention;

FIGS. 3(a) and 3(b) illustrate the direct relationship between the spin-lattice T1 relaxation times at two different magnetic field strengths for the phantom of FIG. 1 as measured by a reference MRI experiment and a clinically-practicable MRI sequence;

FIGS. 4(a) and 4(b) illustrates how the amount of the observed deviation from the linear relationship between the quantities illustrated in FIGS. 3(a) and 3(b) depends on the spin-spin relaxation time T2 for the phantom of FIG. 1;

FIG. 5 illustrates a protocol for quality assurance of T1-mapping;

Figure 7A:
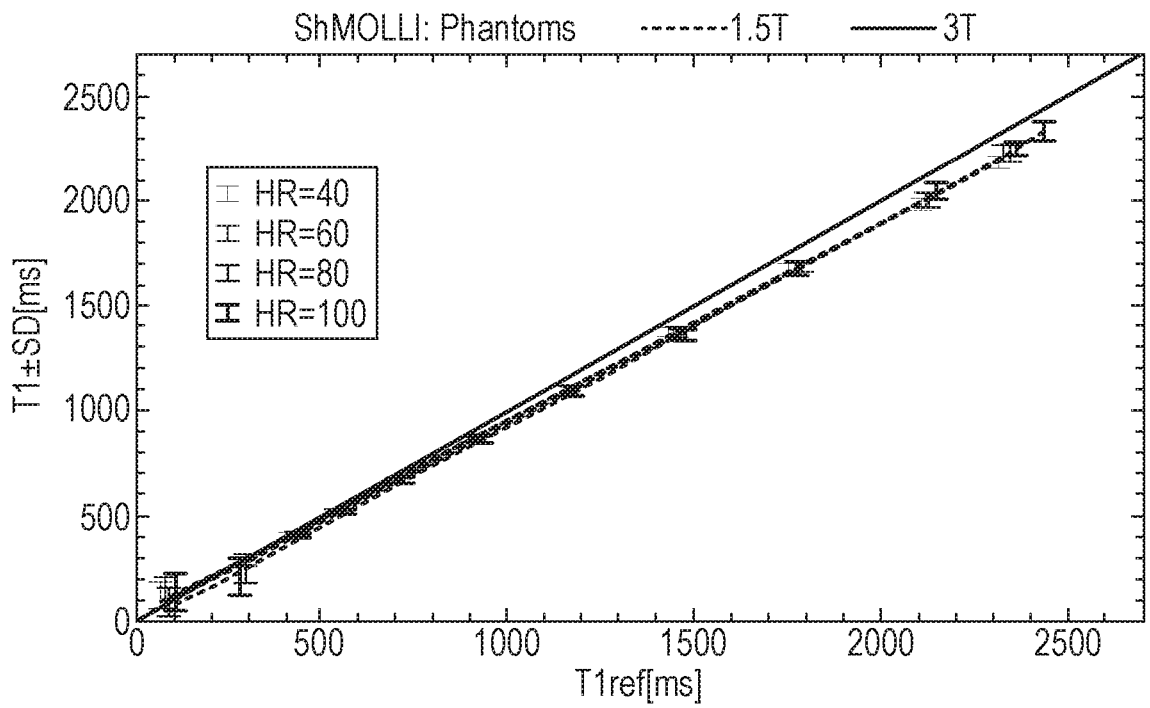
Figure 7B:
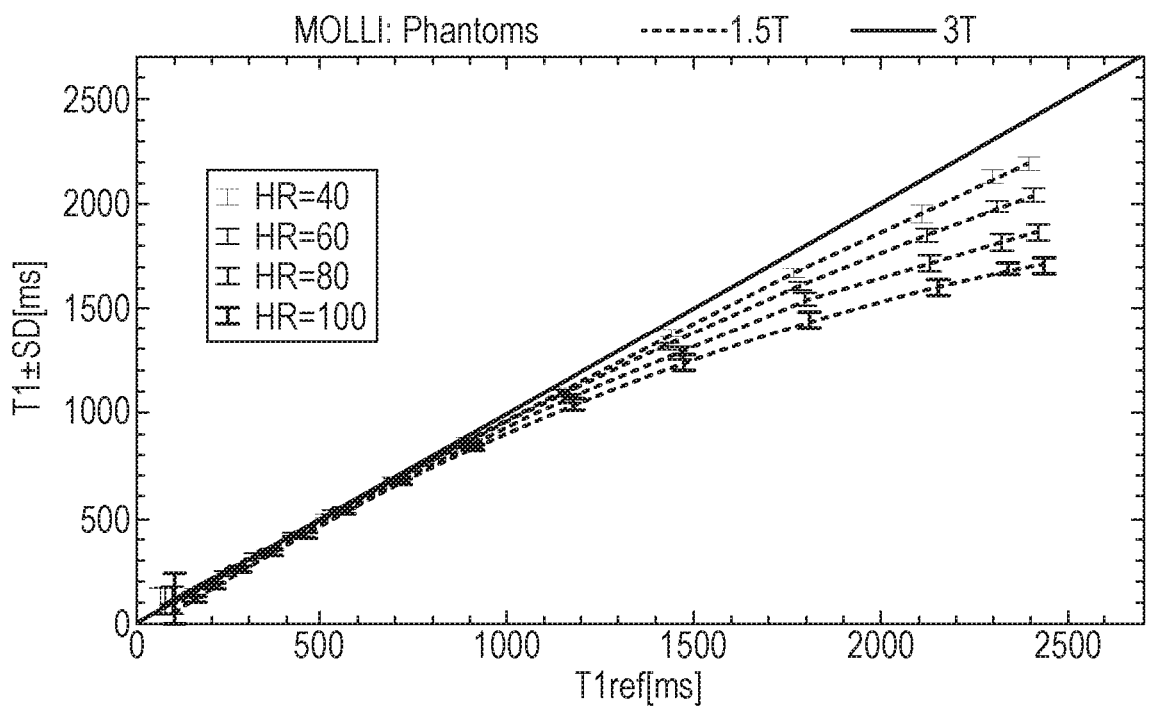
Figure 8:
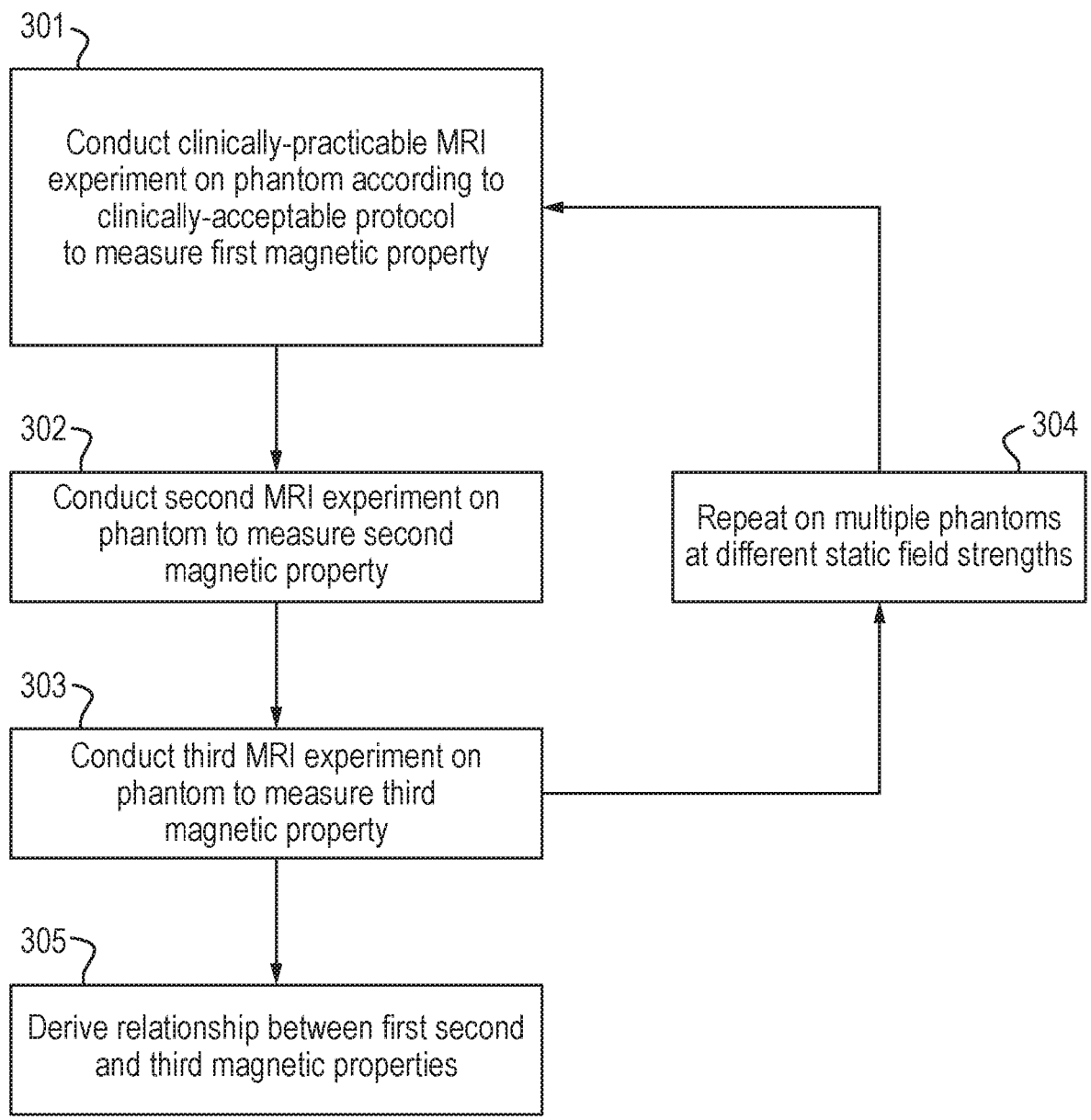
Figure 9:
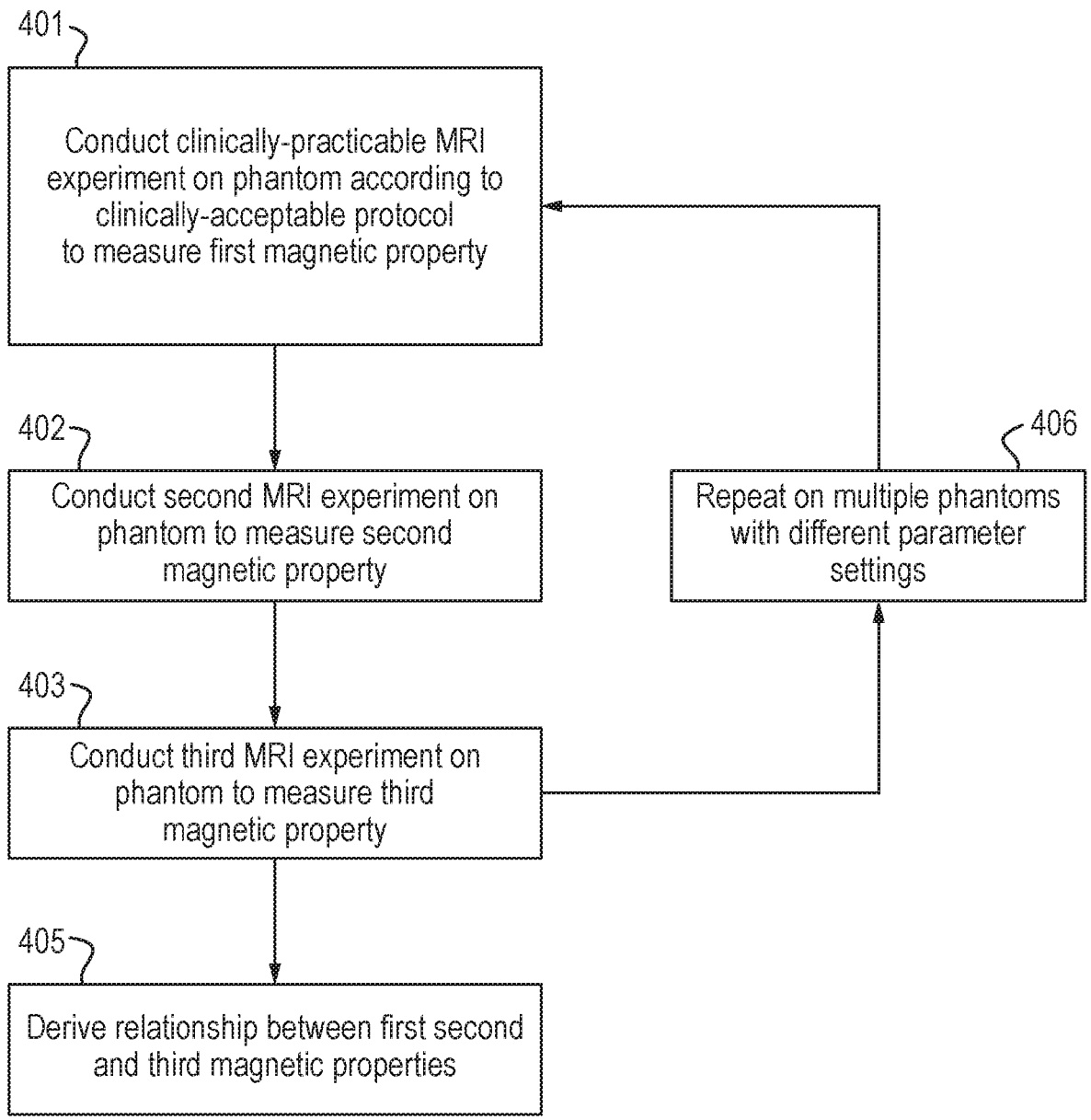
Figure 11A:
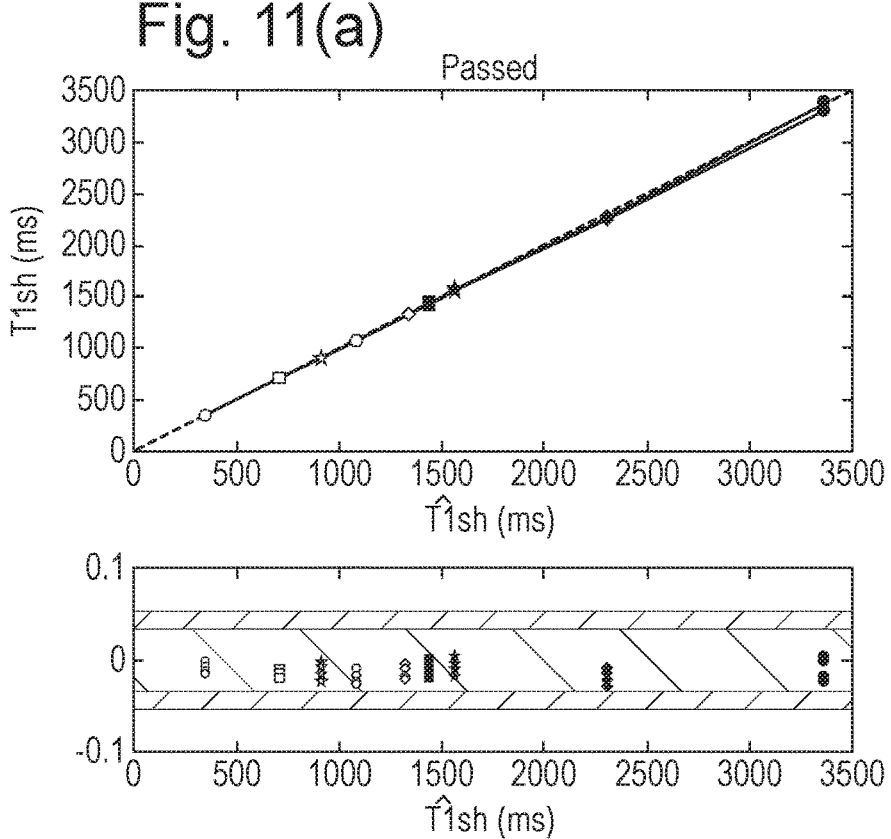
Figure 11B:
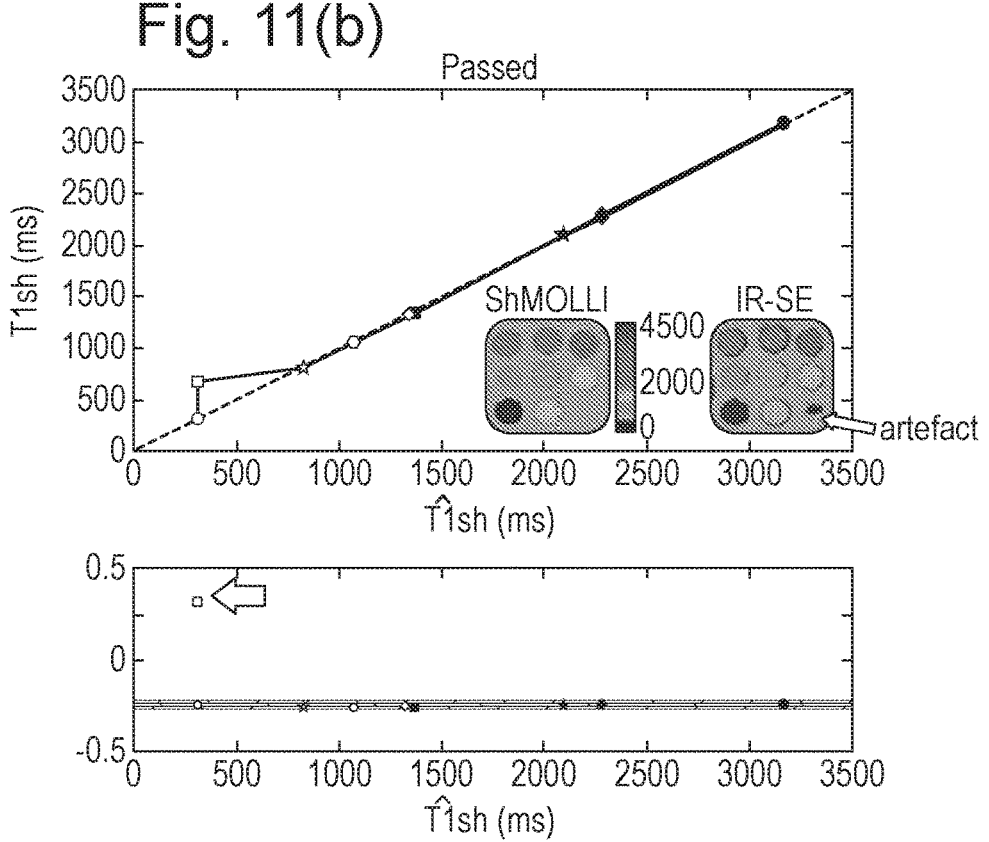
Figure 11E:
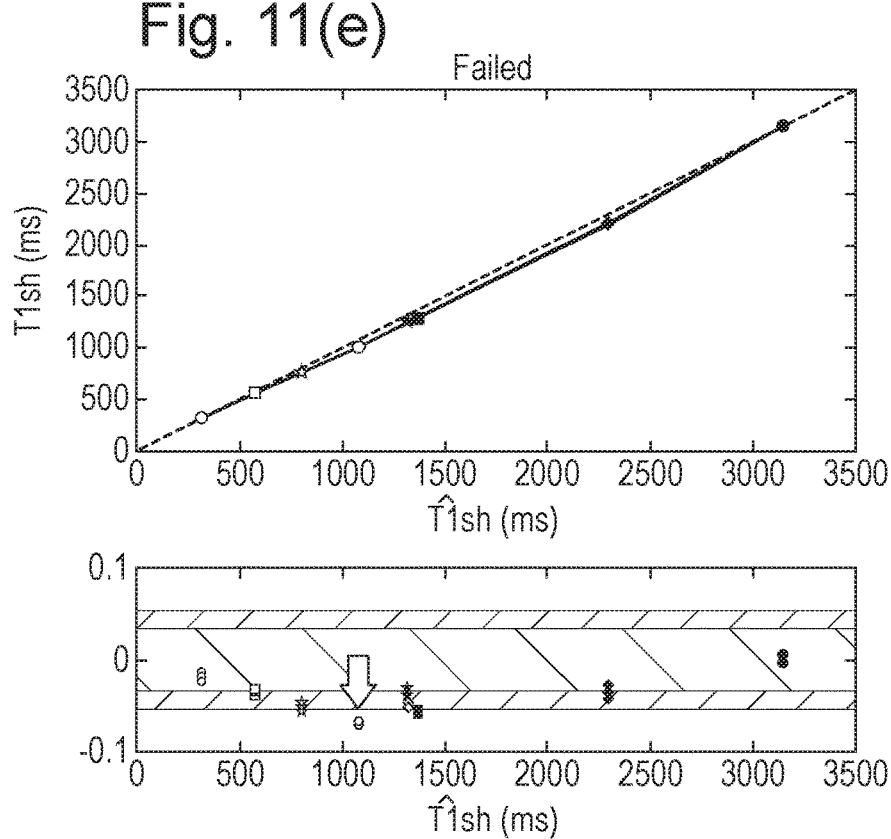
Figure 11F:
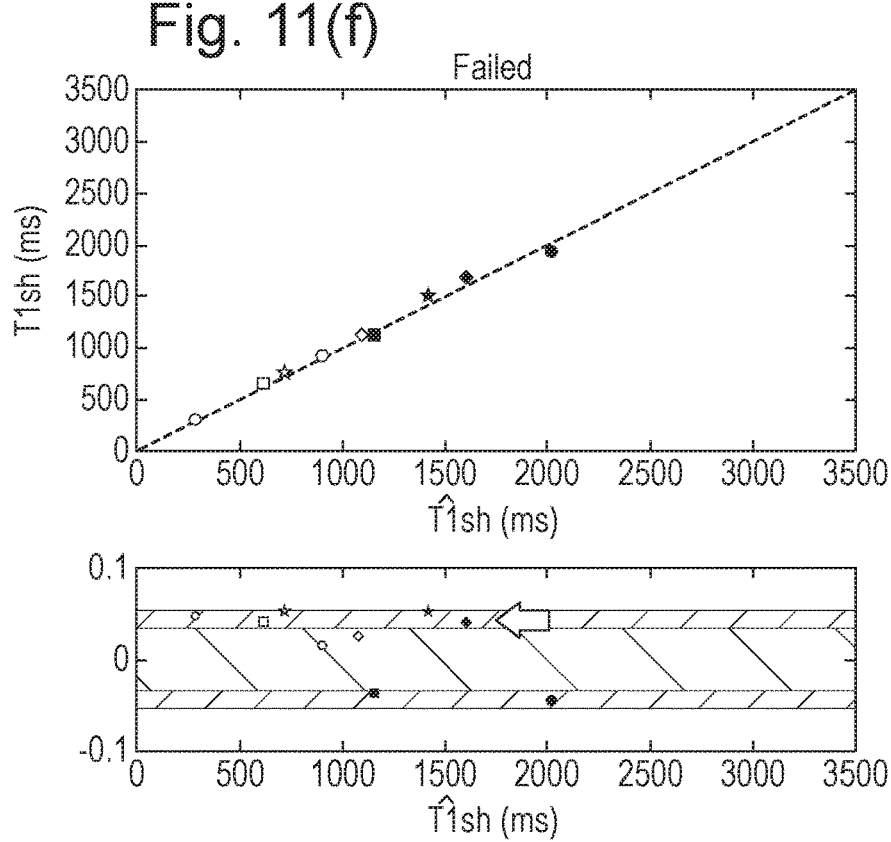

FIGS. 7(a) and 7(b) illustrates potential heart rate dependency profiles arising between different clinically-practicable T1-mapping sequences;

FIG. 8 is a flow diagram illustrating an example of a technique for deriving a relationship between further measured magnetic properties in magnetic resonance imaging;

FIG. 9 is a flow diagram illustrating a further example of deriving the relationship between measured magnetic properties in magnetic resonance imaging;

FIG. 10(a) illustrates the residuals and confidence range for prediction of the clinically-practicable T1 values based on a T2 dependency model established in FIGS. 3(a), 3(b), 4(a) and 4(b);

FIG. 10(b) illustrates additional empirical polynomial correction for the identified trend in the MR model in FIG. 10(a) (shown as dashed line); and FIG. 11 illustrates examples of quality assurance of T1-mapping sequences using phantoms of FIG. 1.

While it may be thought that a way of effectively calibrating the values of magnetic properties measured by an MRI scan would be to measure the magnetic properties of a substance for which the magnetic properties are known (known as a "phantom"), and then apply some calibration factor, it has not been possible to find a substance whose magnetic properties are sufficiently stable and consistent over the desired range of values to allow this in a cost-effective way.

The inventors have found that if clinically-practicable, i.e. accelerated, MRI protocols are followed properly the normal values between various scanners are the same and potentially allow direct comparison of pathological departures. From MR theory there should further be a consistent relationship between the magnetic properties measured by the clinically-practicable sequence and the magnetic properties measured by reference sequences. The relationship should have a general form, i.e independent of the exact specification of the properties of what is being measured. However, while multiple simulations using the Bloch equations that govern MR physics can be performed to guide understanding of such dependencies there is no guarantee these can fully describe the relationship due to the need to assume many unknown factors.

The inventors have found that instead (notwithstanding, and utilising any theoretical background if possible) it is possible to establish such a relationship experimentally. This means that the MRI scans can be conducted on a relatively simple phantom and regardless of the history or nature of the phantom, it is possible to determine whether a clinically-practicable MRI protocol has been followed by comparing the measurements of the magnetic property using that protocol to reference measurements made on a similar phantom. The phantom does not have to be exactly the same, but only span a reasonably similar range of properties required to establish and validate the MR model. It is therefore possible to quality-assure MRI results from a particular scanning centre by requiring that scanning centre to regularly perform both clinically-practicable MRI measurements and reference measurements on a phantom and comparing the results to check that they have the required relationship.

Figure 1A:
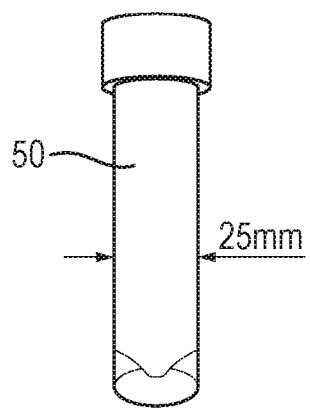
Figure 1B:
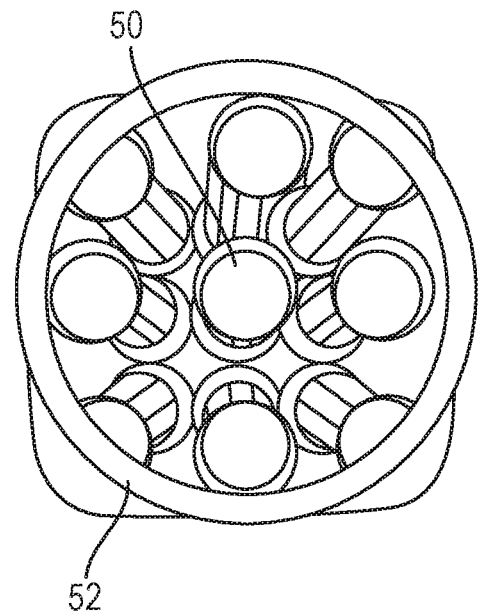
Figure 1C:
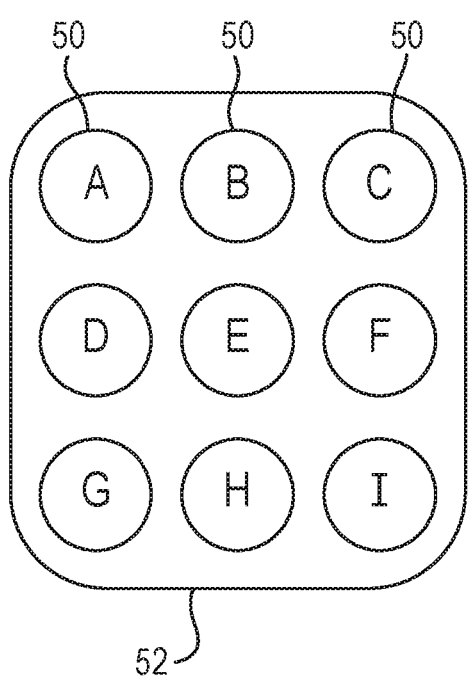
Figure 1D:
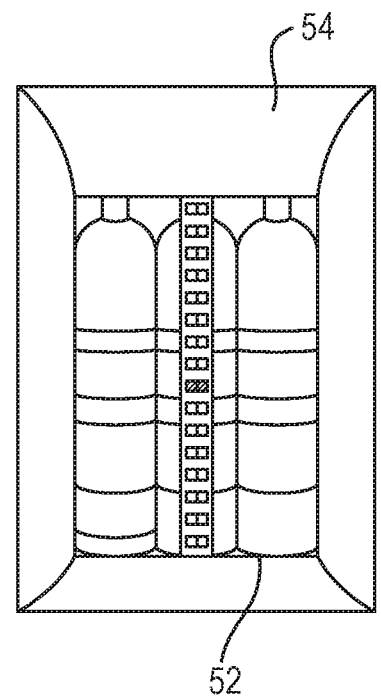

FIGS. 1(a) to 1(d) illustrate an example of a phantom suitable for use in the validation and quality assurance technique of the invention, including each of the methods described below. The phantom has nine compartments 50 each consisting of a clinical sample container filled with water-based gels using agar and carrageenan doped with sodium chloride to achieve desired T1 and T2 combinations in the range of 50-3500 milliseconds. FIG. 1(a) illustrates a single container and FIG. 1(b) shows the nine containers stacked in a 3×3 arrangement in a PCV container 52. This, in turn, is inserted into a tight-fitting cardboard box 54, as shown in FIG. 5(d) to provide some protection from damage and improved internal thermal uniformity. FIG. 1(c) schematically indicates the containers labelled A to I and the characteristics of the contents of the containers are shown in Table 1 below with the achieved T1 and T2 combinations.

TABLE 1

| | | ShMOLLI T1 (mean ± SD) in ms | | T2 (mean ± SD) in ms | |
|---|---|---|---|---|---|
| Phantom compartment and formulation | | 1.5 T (21.3 ± 0.4° C.) | 3 T (21.0 ± 0.5° C.) | 1.5 T (21.0° C.) | 3 T (21.0° C.) |
| A | 0.5% Agar, 0.33% Carrageenan, 0.113 mM $NiCl_2$ | 2529.5 ± 14.0 | 2461.0 ± 7.8 | 275.8 ± 2.1 | 265.9 ± 4.8 |
| B | 0.5% Agar, 0.626 mM $NiCl_2$ | 1396.2 ± 5.9 | 1329.4 ± 2.2 | 266.2 ± 4.6 | 259.0 ± 2.2 |
| C | Undoped 18 MOhm deionized $H_2O$ | 3251.5 ± 12.5 | 3234.9 ± 27.8 | 2373.4 ± 184.3 | 2383.1 ± 153.9 |
| D | 1.9% Agar, 1.2 mM $NiCl_2$ | 859.1 ± 2.9 | 804.71 ± 0.74 | 72.2 ± 0.7 | 71.4 ± 0.4 |
| E | 2% Agar, 0.77 mM $NiCl_2$ | 1109.7 ± 12.5 | 1051.3 ± 1.9 | 69.6 ± 1.2 | 70.7 ± 0.8 |
| F | 2% Agar, 0.524 mM $NiCl_2$ | 1397.8 ± 4.7 | 1328.0 ± 2.2 | 80.2 ± 1.4 | 78.4 ± 2.8 |
| G | 1.5% Agar, 0.1% Carrageenan, 4.5 mM $NiCl_2$ | 323.1 ± 0.66 | 307.5 ± 0.6 | 72.4 ± 0.7 | 68.5 ± 1.1 |
| H | 3% Agar, 0.457 mM $NiCl_2$ | 1428.8 ± 3.9 | 1368.1 ± 3.4 | 56.9 ± 0.4 | 56.5 ± 2.6 |
| I | 1.8% Agar, 2 mM $NiCl_2$ | 610.2 ± 1.3 | 574.4 ± 0.5 | 74.0 ± 0.7 | 72.5 ± 1.5 |

Figure 2:
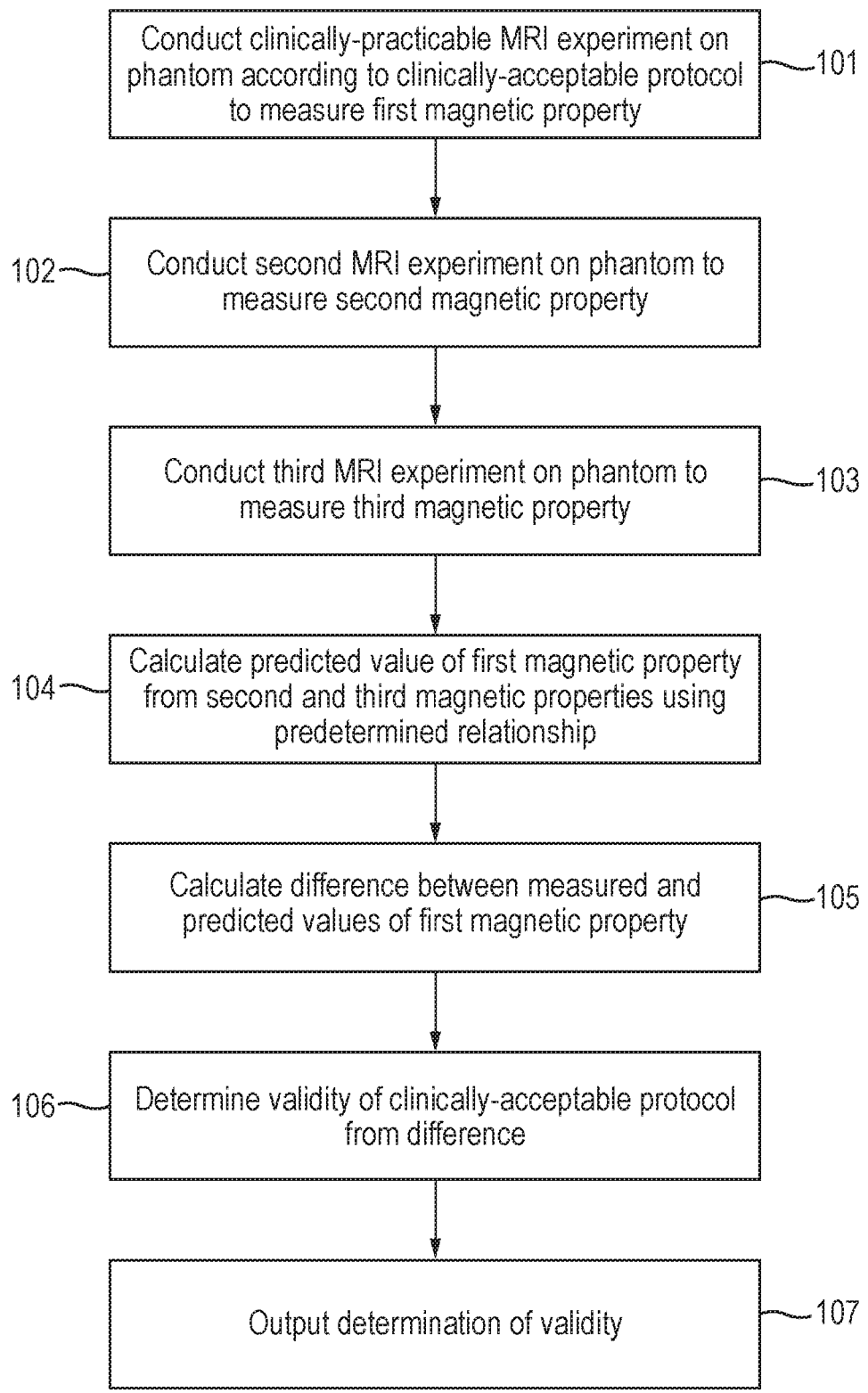

FIG. 2 schematically illustrates the first embodiment of a validation or quality-assurance technique based on this idea. In step 101 a clinically-practicable MRI experiment is conducted on a phantom according to a clinically-practicable protocol in order to measure a first magnetic property.

Figure 3A:
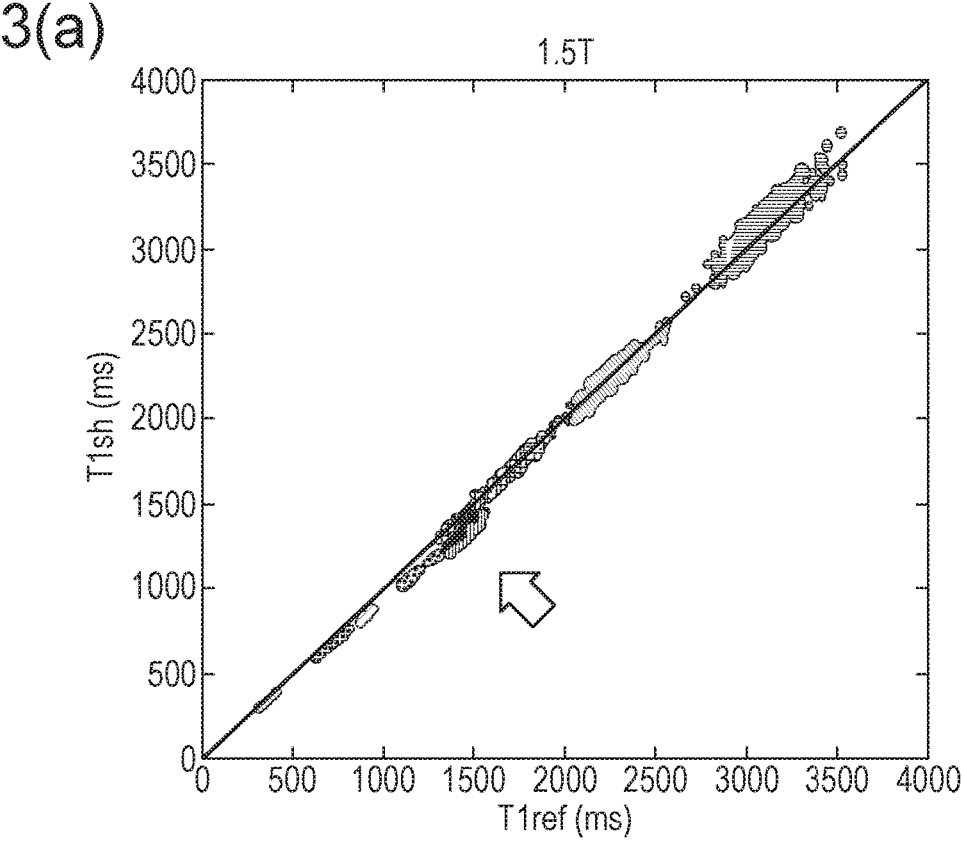
Figure 3B:
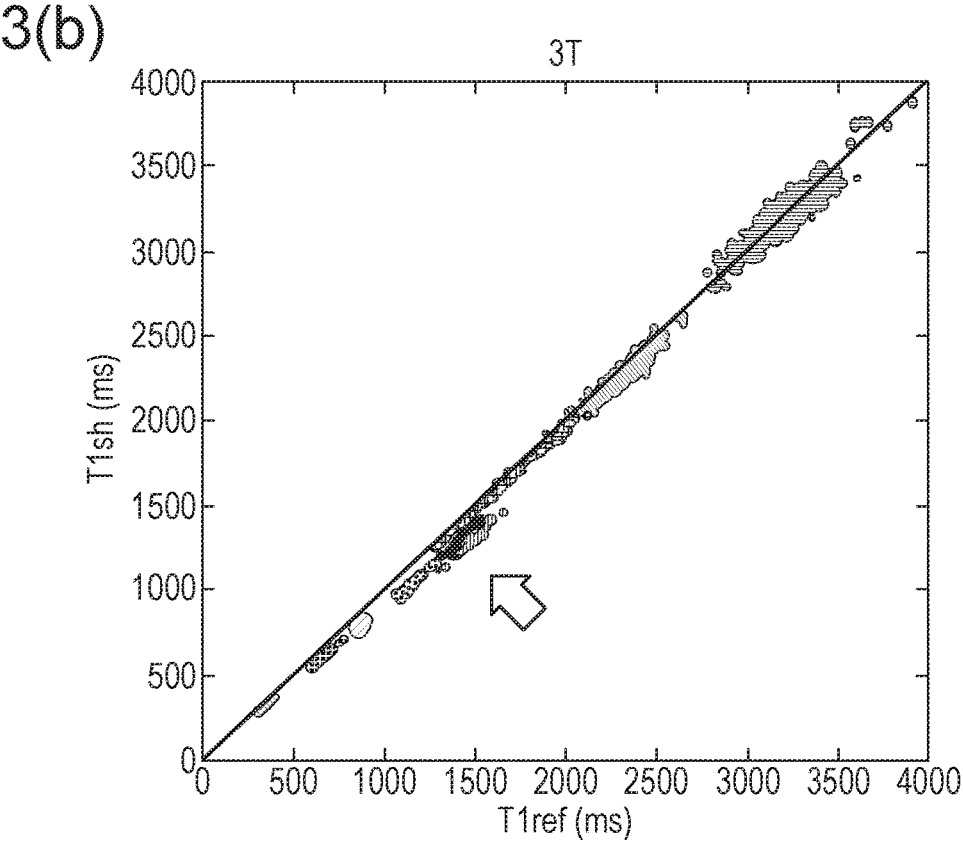

An example of such a clinically-practicable MRI experiment would be ShMOLLI T1-mapping or a MOLLI T1-mapping. This experiment is carried out on a phantom such as that illustrated in FIG. 1, which includes compartments containing substances with a variety of T1 and T2 values, chosen to span the range of interest for the MRI scans. In step 102 a second MRI experiment (consisting of one or more sequences, with appropriate post-processing) is conducted on the phantom to measure a second magnetic property. The second magnetic experiment may be of longer duration, such as slice-selective inversion recovery spin echo sequences to provide reference T1 values of the phantom. As mentioned above, although both the first and second experiments are measuring T1 values, typically the T1 values measured by the accelerated, clinically-practicable sequence differ from those measured by the longer duration reference sequence. The reference sequences are considered to be more standard and thus easier transferrable between various equipment than the accelerated clinical sequences, which have often bespoke proprietary characteristics. FIGS. 3(a) and 3(b) illustrate this difference in T1 values (i.e. between T1sh and T1ref in this example) at two different static field strengths, 1.5 T and 3 T. The intended linear relationship shows deviations related to additional properties (most prominent indicated by the arrows).

In step 103 a third MRI experiment is conducted on the phantom to measure a third magnetic property. This may, for example be a sequence to measure the spin-spin relaxation time T2, such as a multi-echo SE sequence.

Figure 4A:
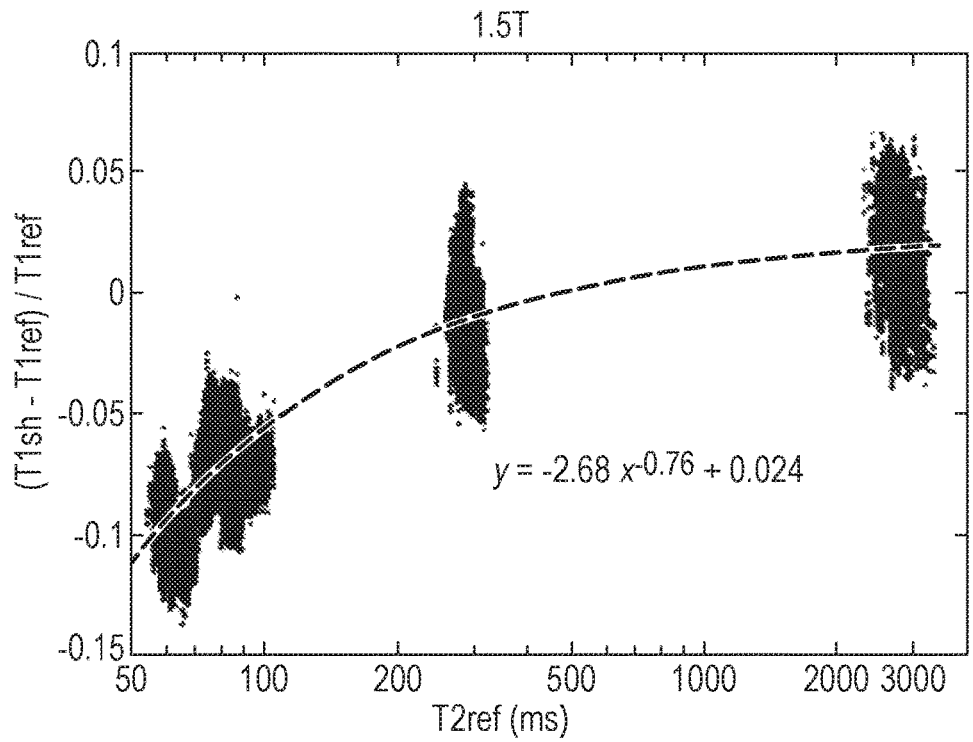

FIGS. 4(a) and (b) illustrate how the deviation between the T1 values measured by the clinically-practicable sequence and the reference experiment depends on T2 at the two different static field strengths used. Note that the relationships are relatively similar and, in some cases may be considered the same and pooled between magnetic field settings, as long as this addresses for the required range of tolerances in sequence identification for clinical application.

Then in step 104 a predicted value of the first magnetic property can be calculated from the measured values of the second and third magnetic properties using a predetermined relationship between the three. If the clinically-practicable protocol has been implemented and followed correctly, there should be little to no difference between the predicted value of the first magnetic property and its measured value. Thus in step 105 the difference is calculated between the measured value of the first magnetic property and the predicted values and in step 106 this difference is compared to a predefined confidence interval to determine whether the clinically-practicable MRI protocol was followed correctly, i.e. being valid if the difference is below a predetermined threshold, and otherwise being not valid.

In step 107 the determined validity is output and may be recorded for certification of the current performance of the scanner. Here and in the corresponding steps of the methods below, the output may be output of data representing the determined validity. The output may be displayed on an display.

Further confidence may be obtained by multiple measurements of any magnetic property measured, as shown in FIG. 5 which is now described.

FIG. 5 illustrates an example of the list of scanning experiments of the first embodiment. Steps 7 to 15 conduct repeated ShMOLLI T1-mapping measurements on a phantom and steps 19 to 30 are used to reconstruct the reference T1 values and steps 17, 18 or 31 are used to reconstruct reference T2 values. In the case of adapting this protocol to allow for variation in other parameters, depending on which of the magnetic properties are affected, steps 7 to 15 or the scanning process would be repeated with different values for those parameters, for example at different ambient temperatures for the whole scanning process or with different heart rate settings for step 7 to 15.

Figure 6:
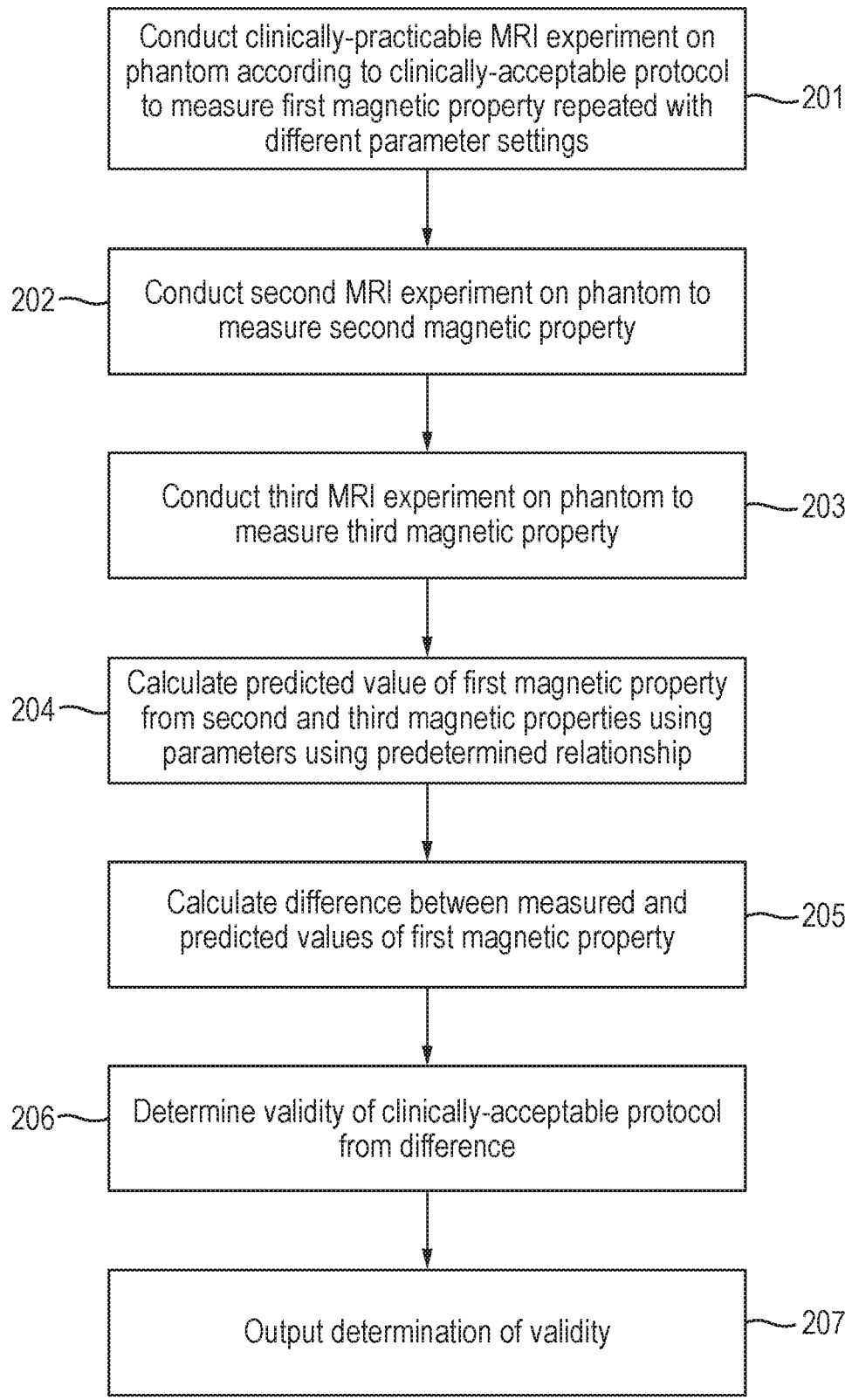
FIG. 6 is a flow diagram illustrating a quality assurance technique according to a second embodiment of the invention.

FIG. 6 illustrates a second embodiment of the invention which is similar to the first embodiment except that in the first embodiment it is assumed that the value of the first magnetic property can be predicted based only on the second and third magnetic properties. However for some clinically-practicable MRI sequences additional parameters may have an effect on this relationship. For example, in the case of the MOLLI T1-mapping sequence, the difference between MOLLI T1 values and reference T1 values has a heart rate dependency as shown in FIGS. 7(a) and 7(b) which illustrates in FIG. 7(a) the lack of heart rate dependency of ShMOLLI compared with the clear heart rate dependency of MOLLI shown in FIG. 7(b). In other clinically-practicable sequences a different parameter or further additional parameters may affect the relationship. Modelling and testing for presence of such patterns may thus require further parameters for full identification of the techniques. The second embodiment takes account of this multi-parameter dependency by repeating the step of performing the clinically-practicable MRI sequence on the phantom with different parameter settings each time. For example, magnetisation transfer could replace or be used in addition to T2 measurements. If there is a heart rate dependency then the clinically-practicable MRI sequence is conducted at different heart rate settings by setting up artificial electrocardiogram to represent various heart rhythms or frequencies.

Some settings and physical properties, although affecting the value of the magnetic property of the phantom, will not affect the relationship. In the first embodiment this has been confirmed for temperature and age of the phantoms. Unless desired for other purpose (e.g. quality control of phantom status, ageing, etc) such parameters excluded from the relationship will not be necessarily measured. An example is the ambient temperature which, in ShMOLLI T1 validation, affects measurements of T1sh and T1ref but the model of the relationship between them does not show a temperature dependency. Similarly can be said about moderate deviations in phantom properties, such as age or physical damage, as long as they do not critically limit the span of parameter values used for validation of the MR model.

In steps 202 and 203 the second and third magnetic properties are measured by reference MRI experiments as with the first embodiment and in step 204 these values, together with the different parameter values used in step 201 are used to predict the value of the first magnetic property. In step 205 this is compared to the measured values and in step 206 the validity of the protocol used for the clinically-practicable MRI sequence is determined based on the difference between the predicted and measured values of the first magnetic quantity, i.e. being valid if the difference is below a predetermined threshold, and otherwise being not valid. In step 207 the determined validity is output and, again, may be recorded as the basis of certification for the scanning protocol.

FIG. 8 illustrates a way of obtaining the required predefined relationship between the first, second and third magnetic properties. In step 301 the clinically-practicable MRI experiment is conducted on a phantom, such as that illustrated in FIG. 1, to obtain measurements of the first magnetic property. In step 302 and 303 the second and third MRI experiments are conducted on the same phantom to measure the second and third magnetic properties. These three steps are then repeated on multiple occasions to exploit natural variation on phantom properties due to ageing and ambient temperature variations, optionally on multiple different examples of the phantom. The repeat number may be potentially reduced by using a more complicated phantom. Then in step 305 the relationship between the three quantities is derived empirically using any pre-existing MR theory, publications or dedicated simulations, and empirical data fitting (least square and robust approaches). The relationship effectively constitutes a fingerprint prediction MR model that can be used to predict the first magnetic quantity given measurements of the second and third, and any relevant parameters.

FIG. 9 illustrates the corresponding process where additional parameters are accounted for by conducting the repeats of steps 401, 402 and 403 with different parameter settings. Steps 401 to 405 of FIG. 9 correspond otherwise to steps 1 to 3 of FIG. 8 and are thus not discussed in more detail. In step 404 the other parameters which affect the relationship between the three magnetic properties are varied. For example, in the case of the first magnetic property being MOLLI T1 there is a heart rate dependency. This is modelled in the process of FIG. 9 by varying an artificial electrocardiogram signal during the measurements on the phantom in step 401. It should be understood that the technique extends to a model incorporating more than three magnetic properties, in which case additional experiments similar to step 403 are added to measure the additional magnetic properties.

Figure 4B:
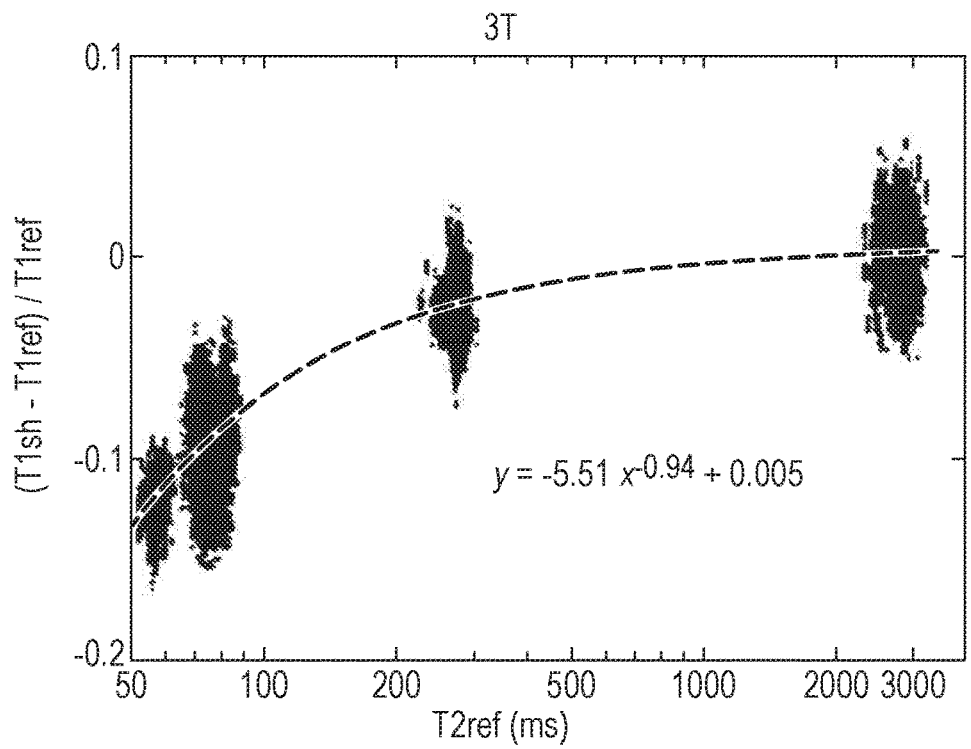

An example of the relationship or prediction model in the case of the ShMOLLI T1-mapping sequence as an example of the clinically-practicable experiment is given below for two different magnetic field strengths (1.5 T and 3 T, being those typically used in clinical practice). As can be seen T1sh generally follows a linear relationship with T1ref but with some known dependency on T2 as illustrated in FIGS. 4(a) and 4(b), fitted as exponential. Correcting for this gives residual errors as indicated in FIG. 10(a), which includes a visible small trend that can be further compensated for using a third order polynomial (the black dashed line arrowed in FIG. 10(a)) to achieve a unity correlation between T1sh and T1ref. The final model predicting the expected T1sh from the reference T1 and T2 measurements in this case is:

$$\widetilde{T1sh} = \begin{cases} T1ref(-2.68*(T2ref)^{-0.76} - 8.21\text{e-}12*T1ref^2 + \\ 4.44\text{e-}8*T1ref^2 - 6.78\text{e-}5*T1ref + 1.052) \text{ at } 1.5T \\ T1ref(-5.50*(T2ref)^{-0.94} - 8.21\text{e-}12*T1ref^2 + \\ 4.44\text{e-}8*T1ref^2 - 6.78\text{e-}5*T1ref + 1.033) \text{ at } 3T \end{cases}$$

This model is therefore an example of the model used in step 104 or 204 to calculate a predicted value of the first magnetic property (T1sh in this particular example) which can be compared to the measured values from step 101 or 201. The measurement can be regarded as valid or non-valid depending on whether it lies within a suitable confidence interval. In FIG. 10(b) the 95% confidence interval is indicated, together with a 99.7% confidence interval and also one standard deviation.

FIG. 11 illustrates the results of an example of conducting a quality assurance program on multiple participating MRI sites. In this case the multiple sites were asked to conduct a validation method in accordance with the first embodiment of FIG. 2 in which the clinically-practicable MRI experiment is a ShMOLLI T1-mapping and the second and third MRI experiments are to measure T1 reference and T2 reference as discussed above. The sites conducted these measurements on phantoms as illustrated in FIG. 5. The sites were provided with protocols (shown in FIG. 11) to perform five repeated ShMOLLI sequences, an IR-SE experiment and a multi-echo SE experiment with the following specifications.

1) Repeated ShMOLLI T1 [10] sequences: echo time (TE)=1.07 ms; repetition time (TR)=3.57 ms; inversion times (TI)=100, 1100, 2100, 3100, 4100, 180, 260 ms; flip angle (FA) 35°; FOV=270×360 mm; matrix size 384×288; slice thickness 8 mm; body matrix coil; GRAPPA×2.
2) Slice-selective IR experiment with a turbo spin-echo readout with turbo factor 7 to provide reference T1 relaxation time: TE=11 ms; TR=10000 ms; TI=33, 100, 300, 900, 2700 and 5000 ms; FOV=360×360 mm; matrix size=256×256; slice thickness 8 mm; body matrix coil.
3) Multi-echo SE experiment to provide reference T2 relaxation time: TE=15-480 ms every 15 ms; TR=9000 ms; FOV=360×360 mm; matrix size 256×256; slice thickness 8 mm; body matrix coil.

Seventy-eight quality assurance scans from twenty-eight scans are categorised in Table 2 below.

TABLE 2

QA results of 78 scans from 28 sites with proposed outcomes and actions.

| QA Results | Description | No. of scans (sites) | Action recommended |
|---|---|---|---|
| 1. Passed | All T1 maps in the scan provided T1sh values within the agreement range with expected $\widetilde{T1}$sh (FIG. 11(a)). | 34 scans (15 sites) | QA passed. No further action required. |
| | Disagreement between T1sh and $\widetilde{T1}$sh in one or more individual compartments; the rest were in the agreement range. The source of error can be identified as artefacts in individual compartments in the reference T1 maps (b). | 3 scans (3 sites) | QA passed. No further action required. |
| 2. Warnings | Underestimated T1sh in individual acquisitions. At least one acquisition is within the agreement range. Incomplete recovery of longitudinal magnetization in individual acquisitions (FIG. 11(c)). | 26 scans (16 sites) | QA assed with warning of possible protocol adherence problems |
| 3. Conditional | T1sh values outside the agreement range; unable to identify source of disagreement. However, accurate T1sh values were successfully restored offline with TOMATO [11] package (FIG. 11(d)). | 7 scans (5 sites) | QA conditional on offline reconstruction. Require re-deployment of ShMOLLI sequence. |

TABLE 2-continued

QA results of 78 scans from 28 sites with proposed outcomes and actions.

| QA Results | Description | No. of scans (sites) | Action recommended |
|---|---|---|---|
| 4. Failed | T1sh values outside the agreement range; unable to identify source of error. Unable to restore accurate T1sh values offline (FIG. 11(e)). | 6 scans (3 sites) | QA not passed. Technical investigation required |
| | QA could not be performed due to missing reference T1 or T2 sequences in the scan. | 2 scans (2 sites) | Incomplete scan. Check protocols and repeat QA. |

Various steps of the method may be implemented using a computer apparatus as follows.

Steps 104-107 of FIG. 1, steps 204-207 of FIG. 6, step 305 of FIG. 8 and step 405 of FIG. 9 may be performed using a computer apparatus. In that case, the results of the MRI experiments performed in the other steps may be input as data to the computer apparatus. Optionally, the computer apparatus may also control the MRI apparatus to perform the other steps.

To achieve this, a computer program capable of execution by the computer apparatus may be provided. The computer program is configured so that, on execution, it causes the computer apparatus to perform the relevant steps of the method.

The computer apparatus, where used, may be any type of computer system but is typically of conventional construction. The computer program may be written in any suitable programming language. The computer program may be stored on a computer-readable storage medium, which may be of any type, for example: a recording medium which is insertable into a drive of the computing system and which may store information magnetically, optically or opto-magnetically; a fixed recording medium of the computer system such as a hard drive; or a computer memory.

The invention claimed is:

1. A method of validating a clinically-practicable MRI protocol comprising the steps of:
    conducting a first, clinically-practicable, MRI experiment on a phantom to measure a first magnetic property of the phantom in accordance with the clinically-practicable MRI protocol to be validated;
    conducting a second, different MRI experiment on the phantom to measure a second magnetic property of the phantom;
    conducting a third MRI experiment on the phantom, the third MRI experiment being different from said first and second MRI experiments, to measure a third magnetic property of the phantom different from said first and second magnetic properties;
    calculating a predicted value of the first magnetic property from the measured second and third magnetic properties on the basis of a predetermined relationship between the first, second and third magnetic properties, wherein the predetermined relationship is previously obtained by performing the measurements of the first, second and third magnetic properties multiple times;
    calculating the difference between the predicted value of the first magnetic property and the measured value of the first magnetic property;
    determining that the MRI protocol used for said first MRI experiment was valid if the difference between the predicted value of the first magnetic property and the measured value of the first magnetic property is below a predetermined threshold; and
    outputting the result of the determination.

2. A method according to claim 1, wherein the predetermined relationship is a non-linear, multi-parameter relationship.

3. A method according to claim 1, wherein the predetermined relationship is obtained by performing the measurements of the first, second and third magnetic properties once or multiple times on each of a plurality of phantoms.

4. A method according to claim 3, wherein the plurality of phantoms varies in at least one of composition and age.

5. A method according to claim 1, wherein the predetermined relationship is obtained by performing the measurements of the first, second and third magnetic properties at two or more different magnetic field strengths.

6. A method according to claim 1, wherein the predetermined relationship is obtained by performing the measurements of the first, second and third magnetic properties at a plurality of different parameter values.

7. A method according to claim 1, wherein the different parameter values comprise at least one of: $T2^*$, diffusion coefficients, temperature, magnetic transfer ratio, coil sensitivity, patient heart rate.

8. A method according to claim 1, wherein the first and second magnetic properties are the same.

9. A method according to claim 8, wherein the first and second magnetic properties are the spin-lattice relaxation time T1.

10. A method according to claim 9, wherein the third magnetic property is the spin-spin relaxation time T2.

11. A method of measuring a first magnetic property of human or animal tissue comprising using an MRI protocol validated in accordance with the method according to claim 1.

12. A method according to claim 11, further comprising characterising the tissue according to the measured first magnetic property.

13. A method according to claim 1, wherein the second and third MRI experiments are performed within a hybrid multiparameter acquisition to obtain any or all reference magnetic properties.

14. A method according to claim 1, wherein the first MRI experiment is performed within a hybrid multiparameter acquisition to obtain a set consisting of several first magnetic properties acquired at once.

15. A computer-readable storage medium storing a computer program capable of execution by a computer apparatus and configured, on execution, to cause the computer apparatus to perform a method of validating a clinically-practicable MRI protocol, the method comprising:
    receiving a first magnetic property of a phantom measured by conducting a first, clinically-practicable, MRI experiment on the phantom in accordance with the clinically-practicable MRI protocol to be validated;

receiving a second magnetic property of the phantom measured by conducting a second, different MRI experiment on the phantom; and receiving a third magnetic property of the phantom different from said first and second magnetic properties measured by conducting a third MRI experiment on the phantom, the third MRI experiment being different from said first and second MRI experiments, calculating a predicted value of the first magnetic property from the measured second and third magnetic properties on the basis of a predetermined relationship between the first, second and third magnetic properties, wherein the predetermined relationship is previously obtained by performing the measurements of the first, second and third magnetic properties multiple times;

calculating the difference between the predicted value of the first magnetic property and the measured value of the first magnetic property;

determining that the MRI protocol used for said first MRI experiment was valid if the difference between the predicted value of the first magnetic property and the measured value of the first magnetic property is below a predetermined threshold; and outputting the result of the determination.

16. A computer apparatus arranged to perform a method of validating a clinically-practicable MRI protocol, the method comprising:

receiving a first magnetic property of a phantom measured by conducting a first, clinically-practicable, MRI experiment on the phantom in accordance with the clinically-practicable MRI protocol to be validated;

receiving a second magnetic property of the phantom measured by conducting a second, different MRI experiment on the phantom; and receiving a third magnetic property of the phantom different from said first and second magnetic properties measured by conducting a third MRI experiment on the phantom, the third MRI experiment being different from said first and second MRI experiments, calculating a predicted value of the first magnetic property from the measured second and third magnetic properties on the basis of a predetermined relationship between the first, second and third magnetic properties, wherein the predetermined relationship is previously obtained by performing the measurements of the first, second and third magnetic properties multiple times;

calculating the difference between the predicted value of the first magnetic property and the measured value of the first magnetic property;

determining that the MRI protocol used for said first MRI experiment was valid if the difference between the predicted value of the first magnetic property and the measured value of the first magnetic property is below a predetermined threshold; and outputting the result of the determination.

\* \* \* \* \*